(12) United States Patent
Hansen

(10) Patent No.: US 6,505,623 B1
(45) Date of Patent: Jan. 14, 2003

(54) HAT-HELD RESPIRATORY MASK

(75) Inventor: Gary L. Hansen, Eden Prairie, MN (US)

(73) Assignee: Mallinckrodt Inc., St. Louis, MO (US)

( * ) Notice: Subject to any disclaimer, the term of this patent is extended or adjusted under 35 U.S.C. 154(b) by 56 days.

(21) Appl. No.: 09/325,770

(22) Filed: Jun. 4, 1999

(51) Int. Cl.[7] .............................................. A62B 18/08
(52) U.S. Cl. ........................... 128/207.11; 128/206.27; 128/204.18
(58) Field of Search ...................... 128/201.11, 206.27, 128/207.11, 207.18, 201.22, 201.24, 204.18; 2/175.1, 195.1, 195.2, 195.6, 209.13

(56) References Cited

U.S. PATENT DOCUMENTS

| | | | | |
|---|---|---|---|---|
| 735,959 A | * | 8/1903 | Folkmar | |
| 1,706,602 A | * | 3/1929 | Drager | |
| 2,671,445 A | * | 3/1954 | Charbonnel | 128/141 |
| 3,491,752 A | * | 1/1970 | Cowley | 128/147 |
| 4,546,496 A | * | 10/1985 | Lewis | 2/171.3 |
| 5,687,715 A | * | 11/1997 | Landis et al. | 128/207.18 |
| 5,878,742 A | * | 3/1999 | Figueredo et al. | 128/201.24 |

* cited by examiner

Primary Examiner—Glenn K. Dawson
Assistant Examiner—Mital Patel
(74) Attorney, Agent, or Firm—Rothwell, Figg, Ernst & Manbeck

(57) ABSTRACT

A respiratory mask is provided according to the invention. The respiratory mask includes a respiratory interface adapted to input and output a gas to a respiratory system of a person, a hat having a substantially semi-hemispheric portion adapted to fit over a head of the person and a brim extending outwardly from at least a front portion of the semi-hemispheric portion, and a hose having a proximal end connected to the respiratory interface and passing through the brim and attached to the semi-hemispheric portion, wherein the brim positions and retains the hose, with a distal end of the hose capable of being connected to a gas supply.

7 Claims, 3 Drawing Sheets

HAT-HELD RESPIRATORY MASK

BACKGROUND OF THE INVENTION

1. Field of the Invention

The present invention relates generally to the field of respiratory masks.

2. Description of the Background Art

A respiratory mask is a device used to deliver a gas or gases to a person. In its simplest form, the respiratory mask includes a respiratory interface, an attaching means, and a gas supply hose. The respiratory mask may be used to deliver any variety of gases, including air or oxygen, and a variety of medicines or treatments.

The respiratory interface is fitted over a nose portion of the face of the person in order to supply a gas to a respiratory system of the person. Preferably, the respiratory interface does not allow a supplied gas to escape. A strap or other attaching means may be fitted over the head of the person. Constant pressure gas is therefore delivered, with the mask also including an exhalation hole or exhaust valve whereby expired carbon dioxide is removed. This is referred to as a continuous positive airway pressure (CPAP) mask.

However, the respiratory mask of the related art has drawbacks in that the attaching means may not securely hold the mask in position, may slip up or down because of the shape of the human head, may contact and chafe the ears of a wearer, and provides a securing force in only a single direction. In addition, related art respiratory masks do not provide any aesthetic benefits or pleasing appearance to the related art respiratory mask.

Therefore, there remains a need in the art for an improved respiratory mask.

SUMMARY OF THE INVENTION

A respiratory mask is provided according to the invention. The respiratory mask comprises a respiratory interface adapted to input and output a gas to a respiratory system of a person, a hat having a substantially semi-hemispheric portion adapted to fit over a head of the person and a brim extending outwardly from at least a front portion of the semi-hemispheric portion, and a hose having a proximal end connected to the respiratory interface and passing through the brim and attached to the semi-hemispheric portion, wherein the brim positions and retains the hose, with a distal end of the hose capable of being connected to a gas supply.

The above and other features and advantages of the present invention will be further understood from the following description of the preferred embodiment thereof, taken in conjunction with the accompanying drawings.

DETAILED DESCRIPTION OF THE PREFERRED EMBODIMENTS

Figure 1:
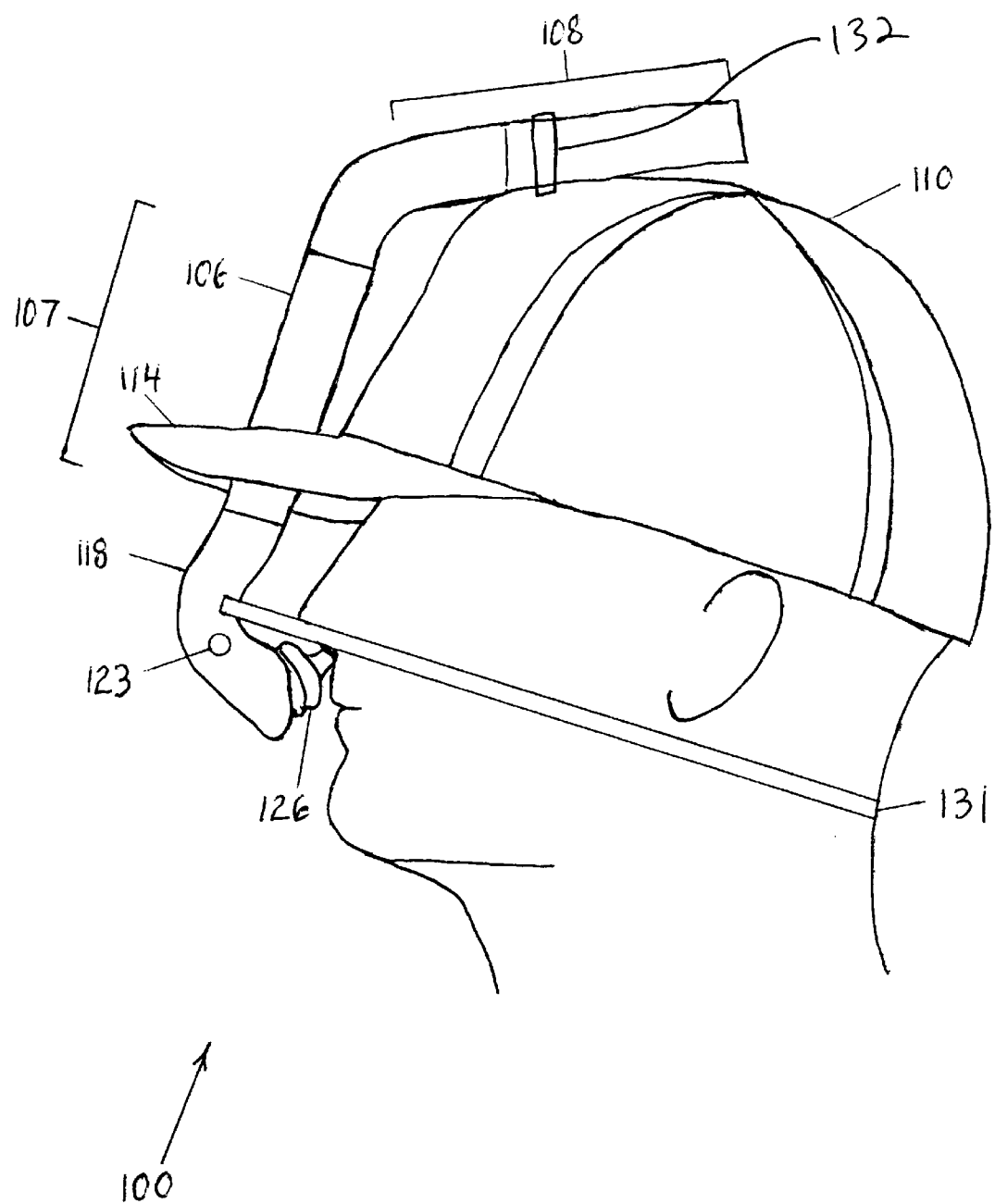
FIG. 1 shows a first embodiment of a respiratory mask and hat of the present invention.

FIG. 1 shows a first embodiment of a respiratory mask and hat 100 of the present invention. The mask 100 includes a hose 106 having a proximal end 107 and a distal end 108, a hat 110 having a brim 114, and a respiratory interface 118 having an exhalation hole 123, at least one nostril insert 126, and an optional elastic strap 131.

A proximal end 107 of the hose 106 passes through the brim 114 of the hat 110. By hat, it is meant any type of substantially semi-hemispheric portion fitting over the head of a person and including a brim 114 extending either partially or completely around the hat 110. In the preferred embodiment, the hat 110 is a baseball cap having a bill 114, but alternatively may be any other type of headgear having some fashion of brim.

In use, the at least one nostril insert 126 is inserted into a nostril of a person wearing the respiratory mask and hat. In the preferred embodiment, two such nostril inserts 126 are used. The nostril inserts 126 allow precise delivery of a gas to the person. The nostril insert 126 may be disposable or may be designed for sterilization to allow for repeated use. The at least one nostril insert 126 is fitted to the respiratory interface 118, which is further fitted to the proximal end 107 of the hose 106. The respiratory interface 118 of the mask 100 is essentially hollow, and provides a connection between the hose 106 and the at least one nostril insert 126 while holding the at least one nostril insert 126 at a proper angle for an essentially leakproof and comfortable fit in a nostril of the person. The respiratory interface 118 may include an exhalation hole or active valve 123, through which expired $CO_2$ is passed to outside the mask.

The distal end 108 of the hose 106 may be connected to an air supply hose (not shown), which may supply a gas or gases or a variety of medicines or treatments.

The respiratory mask 100 is held in position by the hat 110, which provides a stable and secure base. The respiratory mask 100 therefore holds the mask, including the hose 106, securely in place. The hat 110 distributes the weight of the mask 100 over a large area, and therefore makes the mask 100 more comfortable to wear than a mask having only an elastic strap for retaining it. A restraining clip 132 restrains the hose 106 and helps to apply a useful inward force of the mask 100 to the face. The mask 100 may include an optional elastic strap 131, which may provide additional stability to the mask 100 by providing an additional securing force.

In addition, the mask 100 in at least some manner makes a respiratory mask more aesthetically pleasing and less conspicuous. The hat 110 may take on any form or style, and if the hat 110 is a baseball type cap, may include team logos and colors. As an added benefit, the respiratory mask 100 positions an air supply hose over and behind the person, so that the air supply hose is out of the way.

Figure 2:
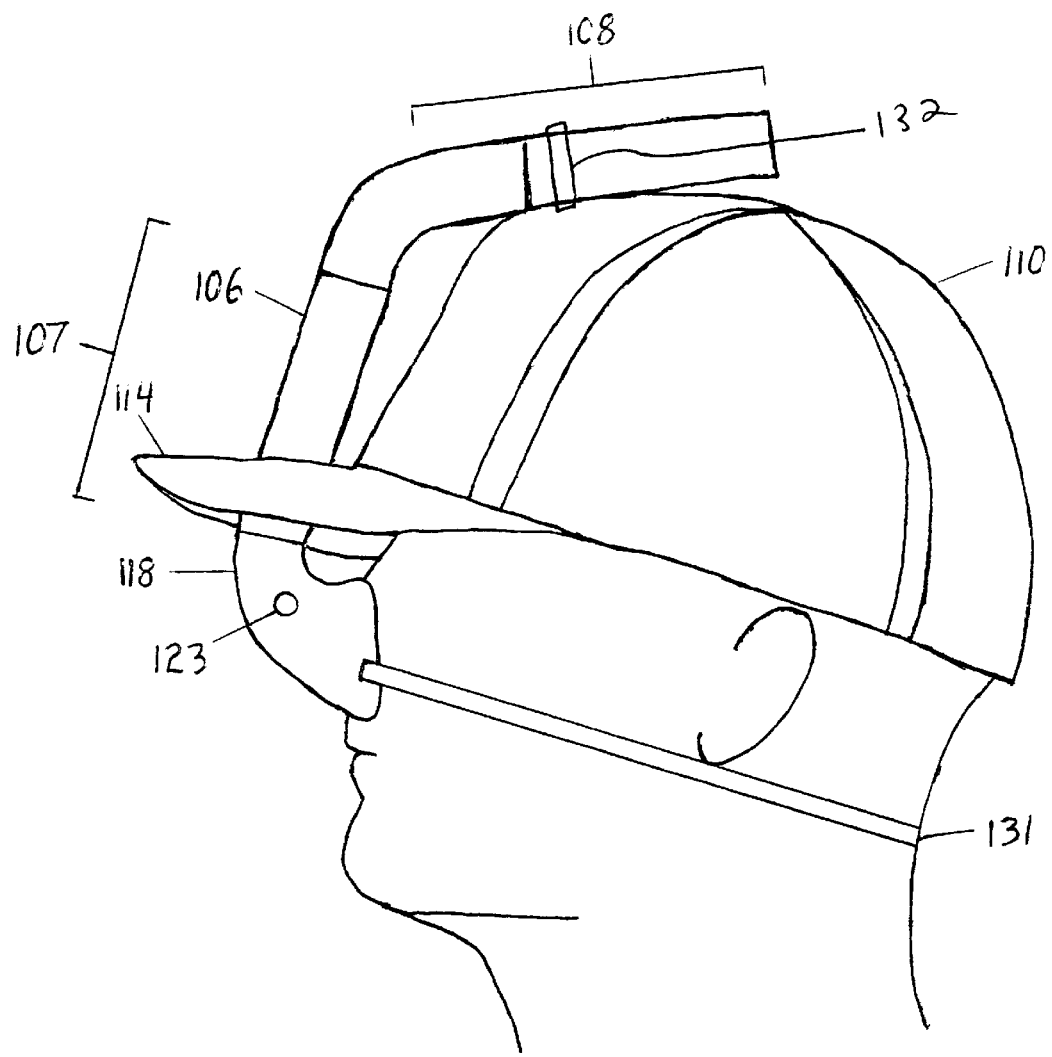
FIG. 2 shows a second embodiment of a respiratory mask and hat of the present invention.

FIG. 2 shows a second embodiment of a respiratory mask and hat 200 of the present invention. The mask 200 includes the same components as the mask 100 except for the lack of the at least one nostril insert 126. Instead of the at least one nostril insert 126, the mask 200 has a respiratory interface 118 which fits over a nose of a person. The fit is essentially airtight, and a gas is therefore delivered to a respiratory system of the person.

Figure 3:
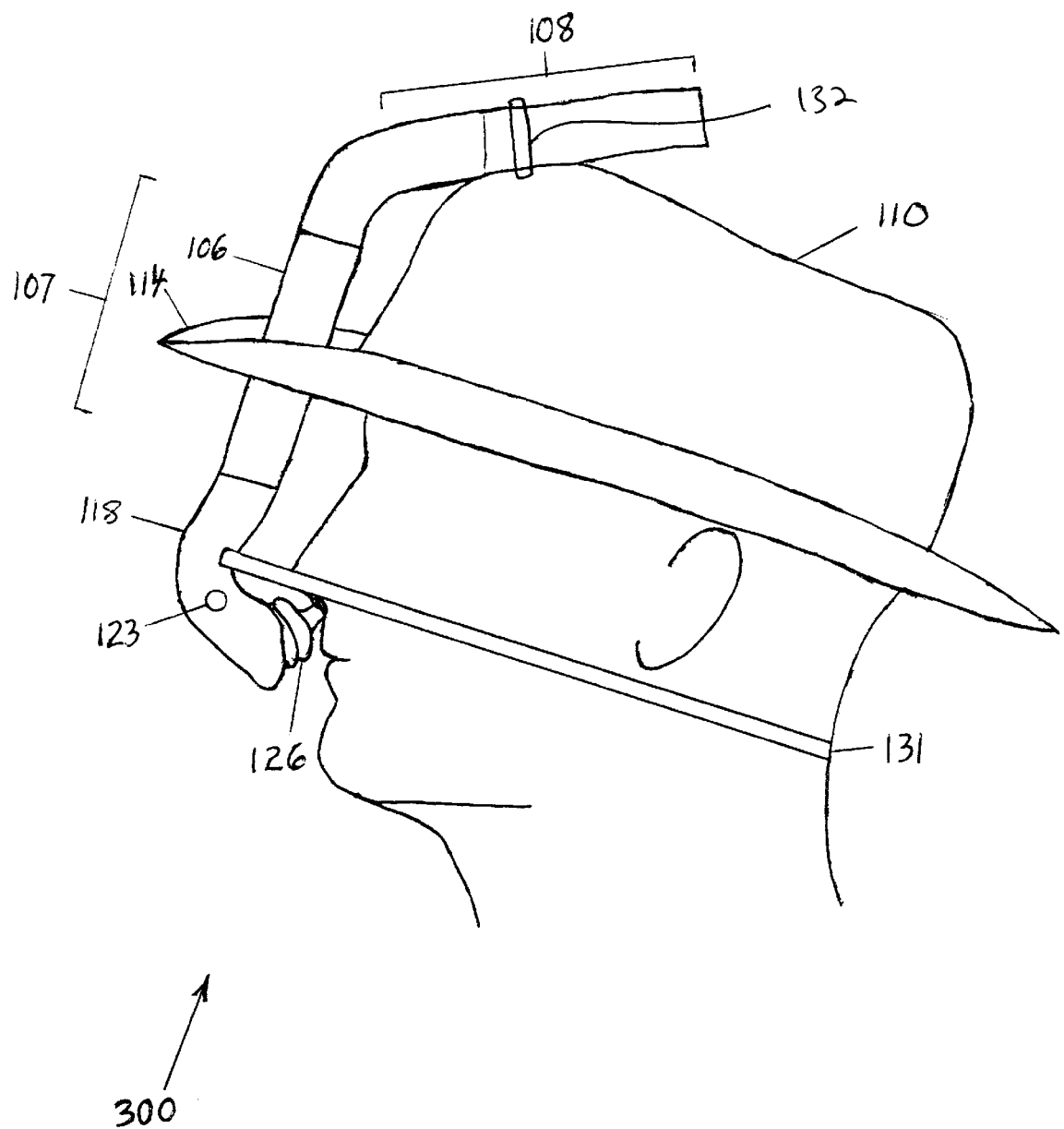
FIG. 3 shows a third embodiment of a respiratory mask and hat of the present invention.

FIG. 3 shows a third embodiment of a respiratory mask and hat 300 of the present invention. In this embodiment, the hat 110 has a continuous brim 114 that extends completely around the hat 110. As discussed previously, it is contemplated that any type of headgear having some form of brim or bill is encompassed by the present invention.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A respiratory mask, comprising:
   a respiratory interface adapted to engage the face of a person and supply a gas to a respiratory system of the person;
   a hat having a substantially semi-hemispheric portion adapted to fit over a head of the person and a brim extending outwardly from at least a front portion of said semi-hemispheric portion; and
   a hose having a proximal end connected to said respiratory interface and passing through said brim and attached to an outer surface of said semi-hemispheric portion;
   wherein said brim positions and retains said hose, with a distal end of said hose capable of being connected to a gas supply.

2. The respiratory mask of claim 1, wherein said respiratory interface is a cup that fits over nostrils of a person.

3. The respiratory mask of claim 1, wherein said respiratory interface further includes at least one nostril insert.

4. The respiratory mask of claim 1, wherein said respiratory interface further includes an exhalation hole or a valve through which expired $CO_2$ is passed to outside the mask.

5. The respiratory mask of claim 1, wherein said hose extends over said semi-hemispheric portion of said hat.

6. The respiratory mask of claim 1, wherein said respiratory interface further includes an elastic strap attached to each side of said respirator interface and provides additional retaining force to said respiratory mask.

7. The respiratory mask of claim 1, wherein said hat is a cap with a bill and said hose passes through said bill.

* * * * *